US012714292B2

(12) United States Patent
Harada

(10) Patent No.: US 12,714,292 B2
(45) Date of Patent: Aug. 25, 2026

(54) OPTICAL UNIT AND ENDOSCOPE

(71) Applicant: OLYMPUS MEDICAL SYSTEMS CORP., Tokyo (JP)

(72) Inventor: Junya Harada, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 292 days.

(21) Appl. No.: 18/659,320

(22) Filed: May 9, 2024

(65) Prior Publication Data

US 2024/0293011 A1 Sep. 5, 2024

Related U.S. Application Data

(63) Continuation of application No. PCT/JP2021/041420, filed on Nov. 10, 2021.

(51) Int. Cl.
*A61B 1/00* (2006.01)

(52) U.S. Cl.
CPC ...... *A61B 1/00165* (2013.01); *A61B 1/00117* (2013.01); *A61B 1/00133* (2013.01); *A61B 1/00158* (2013.01)

(58) Field of Classification Search
CPC ............ A61B 1/00165; A61B 1/00117; A61B 1/00133; A61B 1/00096; G02B 7/04
See application file for complete search history.

(56) References Cited

U.S. PATENT DOCUMENTS

2013/0314517 A1* 11/2013 Makiyama ............. A61B 1/045 348/65
2019/0271825 A1* 9/2019 Kawanabe ............... G02B 7/02

FOREIGN PATENT DOCUMENTS

JP 2006227062 A 8/2006
JP 2013210420 A 10/2013
JP 2014197067 A 10/2014
JP 6678163 B2 4/2020

OTHER PUBLICATIONS

International Search Report dated Dec. 21, 2021 received in PCT/JP2021/041420.

* cited by examiner

*Primary Examiner* — Jason M Ip
(74) *Attorney, Agent, or Firm* — Scully, Scott, Murphy & Presser, P.C.

(57) ABSTRACT

An optical unit includes: a fixed portion; a movable portion arranged movably inside the fixed portion; a first slider arranged between the fixed portion and the movable portion, the first slider being configured to slide with a movement of the movable portion; a second slider arranged between the fixed portion and the movable portion, and at a position different from a position of the first slider, the second slider being configured to slide with the movement of the movable portion; a driver that includes a coil and a magnet; and a biasing part that is arranged outside the movable portion, the biasing part being configured to cause the magnet to generate a biasing force to push the movable portion toward the fixed portion.

20 Claims, 16 Drawing Sheets

OPTICAL UNIT AND ENDOSCOPE

CROSS-REFERENCE TO RELATED APPLICATION

This application is a continuation of International Application No. PCT/JP2021/041420, filed on Nov. 10, 2021, the entire contents of which are incorporated herein by reference.

BACKGROUND

1. Technical Field

The present disclosure relates to an optical unit and an endoscope.

2. Related Art

In the related art, a technique that has a movable portion in which a movable lens is arranged, and that utilizes an electromagnetic actuator using a coil and a magnet, namely a voice coil motor, as a zoom function to change magnification ratios by moving the movable lens portion back and forth relative to a fixed portion and a focusing function for adjusting focus has been disclosed (for example, Japanese Patent No. 6678163).

SUMMARY

In some embodiments, an optical unit includes: a fixed portion having a cylindrical shape; a movable portion holding a lens, the movable portion being arranged movably inside the fixed portion; a first slider that is arranged between the fixed portion and the movable portion, the first slider being configured to slide with a movement of the movable portion; a second slider that is arranged between the fixed portion and the movable portion, and at a position different from a position of the first slider, the second slider being configured to slide with the movement of the movable portion; a driver that includes a coil and a magnet, the driver being configured to move the movable portion in a direction of an optical axis of the lens relative to the fixed portion; and a biasing part that is arranged outside the movable portion, the biasing part being configured to cause the magnet to generate a biasing force to push the movable portion toward the fixed portion. The fixed portion includes a first rail portion and a second rail portion guiding a movement of the first slider and the second slider, respectively, and extending in a direction of the optical axis, the biasing part is arranged at a position facing the second rail portion through the optical axis of the lens, the first slider abuts on the first rail portion, and is pushed in a direction horizontal to the biasing force, and the second slider abuts on the second rail portion, and is pushed in a direction perpendicular to the biasing force.

In some embodiments, provided is an endoscope configured to be inserted into an inside of a subject to observe the inside of the subject. The endoscope includes: an optical unit; an imager configured to convert light guided by the optical unit into an electrical signal; and a controller configured to control driving of the optical unit. The optical unit includes: a fixed portion having a cylindrical shape; a movable portion holding a lens, the movable portion being arranged movably inside the fixed portion; a first slider that is arranged between the fixed portion and the movable portion, the first slider being configured to slide with a movement of the movable portion; a second slider that is arranged between the fixed portion and the movable portion, and at a position different from a position of the first slider, the second slider being configured to slide with the movement of the movable portion; a driver that includes a coil and a magnet, the driver being configured to move the movable portion in a direction of an optical axis of the lens relative to the fixed portion; and a biasing part that is arranged outside the movable portion, the biasing part being configured to cause the magnet to generate a biasing force to push the movable portion toward the fixed portion. The fixed portion includes a first rail portion and a second rail portion guiding a movement of the first slider and the second slider, respectively, and extending in a direction of the optical axis, the biasing part is arranged at a position facing the second rail portion through the optical axis of the lens, the first slider abuts on the first rail portion, and is pushed in a direction horizontal to the biasing force, and the second slider abuts on the second rail portion, and is pushed in a direction perpendicular to the biasing force.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 4 is a plan view illustrating the configuration of the optical unit according to the first embodiment of the disclosure;

DETAILED DESCRIPTION

First Embodiment

Figure 1:
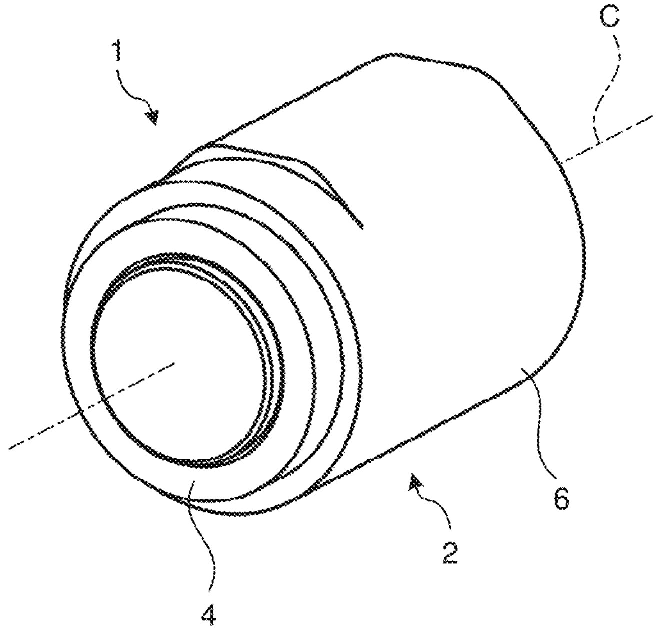
FIG. 1 is a perspective view illustrating a configuration of an optical unit according to a first embodiment of the disclosure.
Figure 2:
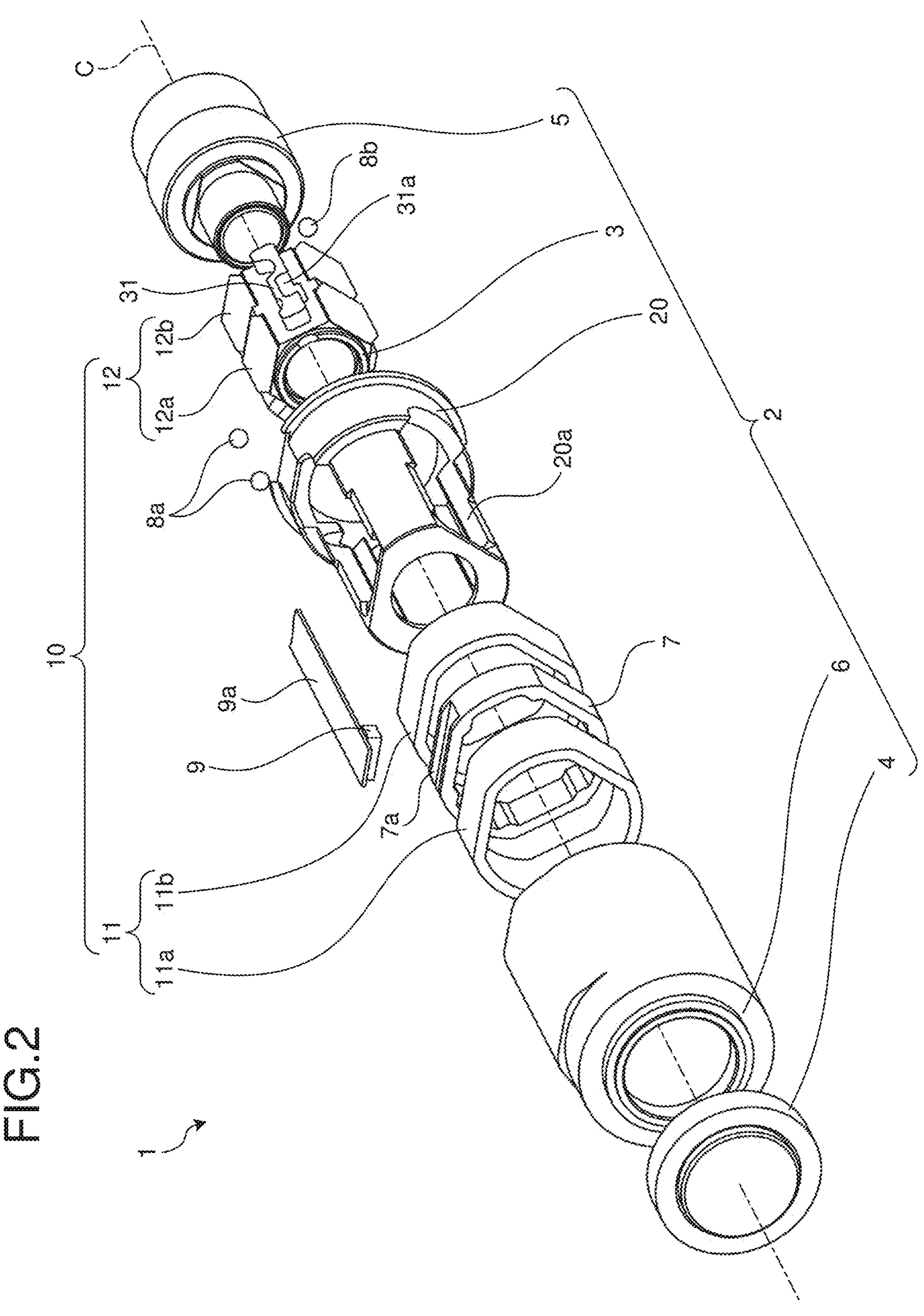
FIG. 2 is a exploded perspective view (Part 1) illustrating a configuration of the optical unit according to the first embodiment of the disclosure.
Figure 3:
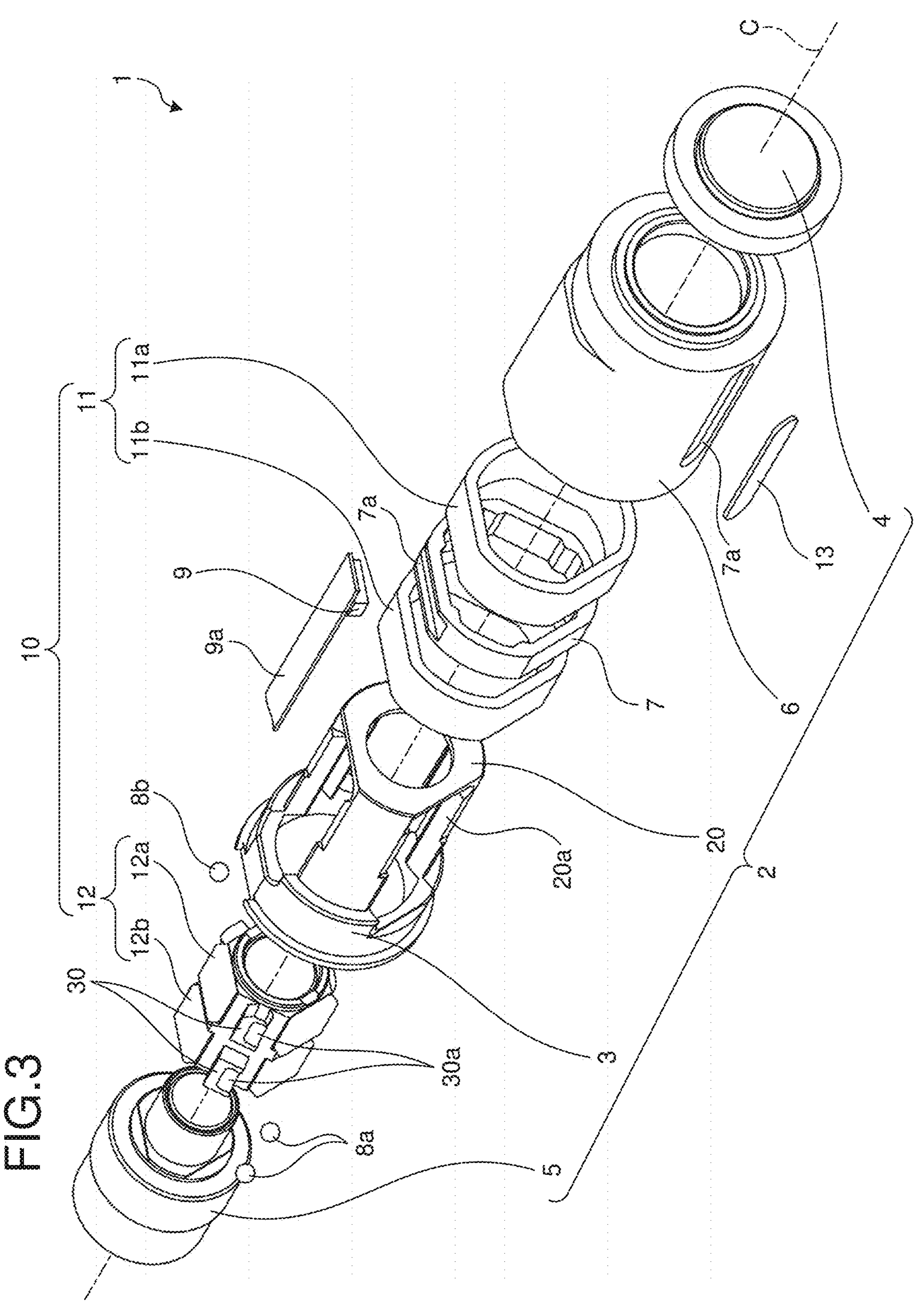
FIG. 3 is a exploded perspective view (Part 2) illustrating a configuration of the optical unit according to the first embodiment of the disclosure.
Figure 4:
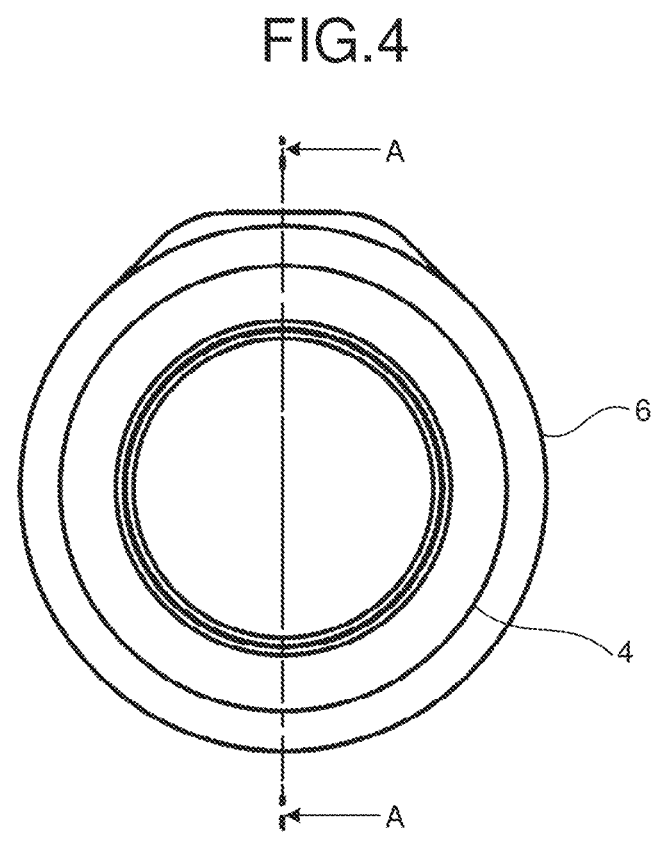
Figure 5:
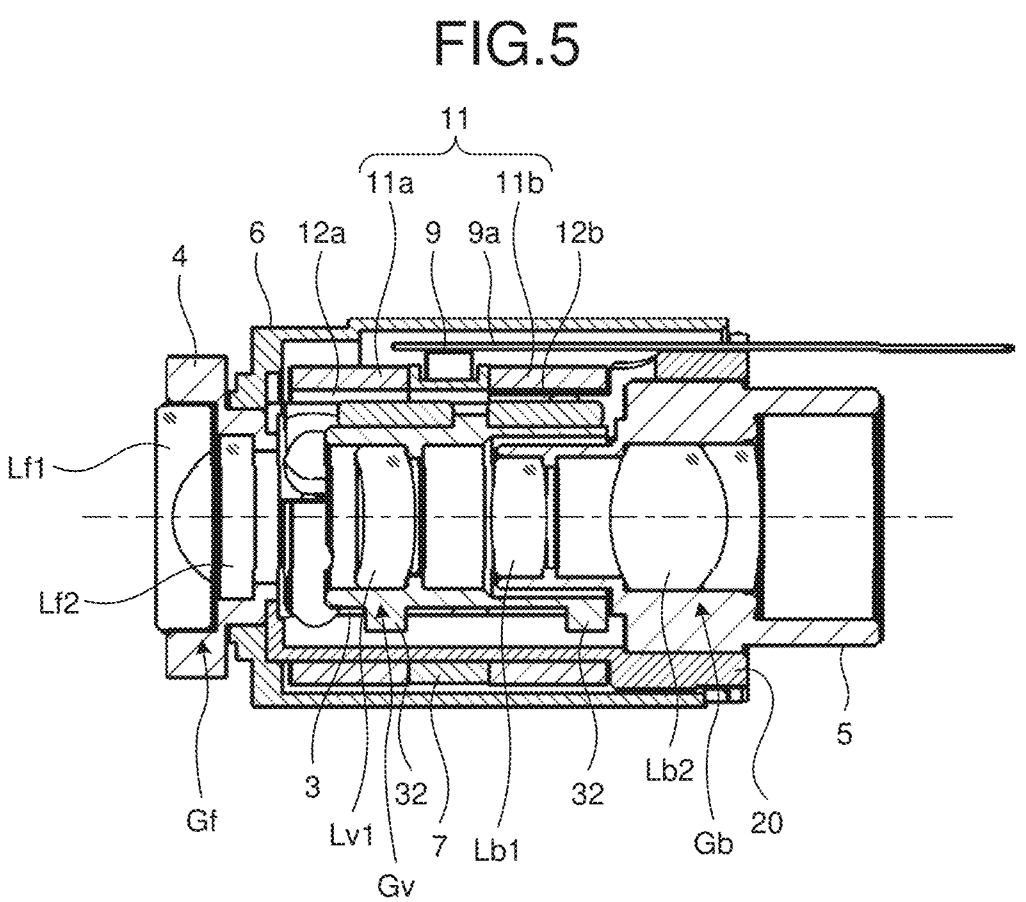
FIG. 5 is an A-A cross-section (Part 1) of the optical unit illustrated in FIG. 4.
Figure 6:
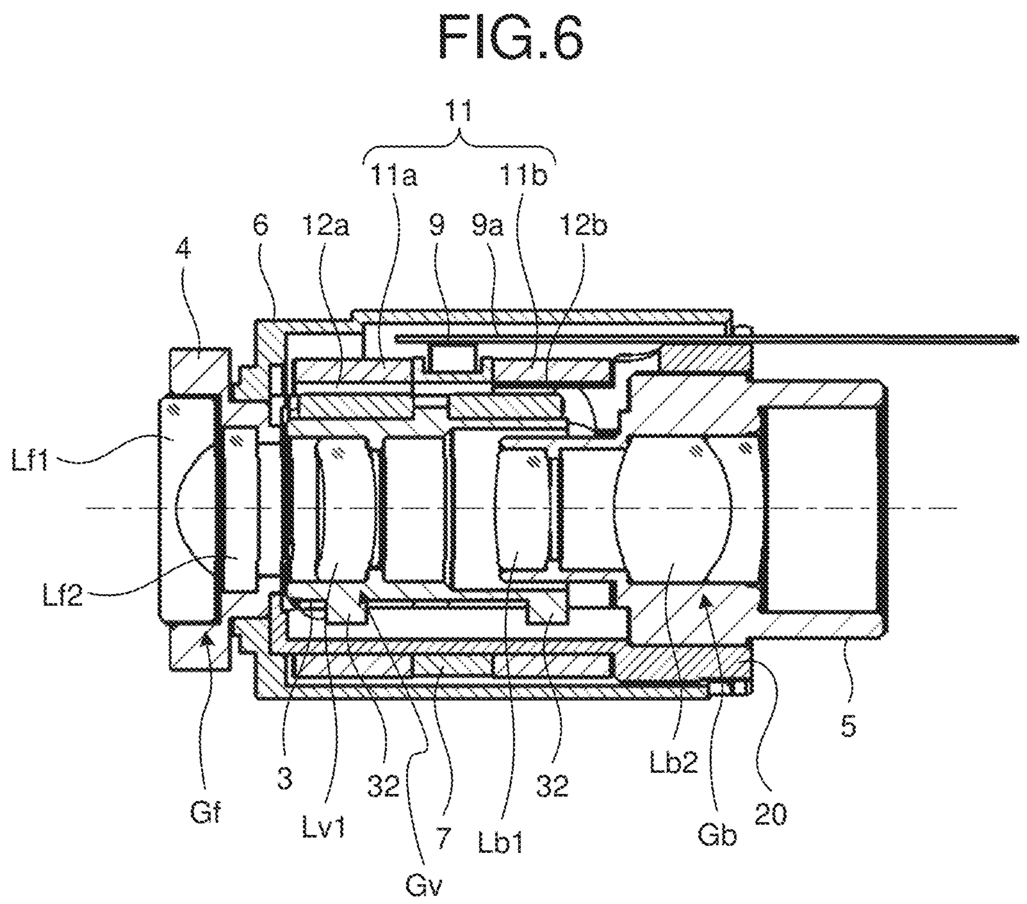
FIG. 6 is an A-A cross section (Part 2) of the optical unit illustrated in FIG. 4.

FIG. 1 is a perspective view illustrating a configuration of an optical unit according to a first embodiment of the disclosure. FIG. 2 and FIG. 3 are exploded perspective views illustrating the configuration of the optical unit according to the first embodiment of the disclosure. FIG. 4 is a plan view illustrating the configuration of the optical unit according to the first embodiment of the disclosure. FIG. 5 and FIG. 6 are A-A cross-sections of the optical unit illustrated in FIG. 4. FIG. 5 illustrates an example when a movable portion 3 moves toward an image side. FIG. 6 illustrates an example when the movable portion 3 moves toward an object side.

An optical unit 1 includes a fixed portion 2, the movable portion 3 that is movable relative to the fixed portion 2, and a voice coil motor 10 that generates a driving force to move the movable portion 3 relative to the fixed portion 2. Hereinafter, an example in which an axis C passing through the optical unit 1 coincides with an optical axis of the optical unit 1 will be explained. Hereinafter, an opposite side to the object side in a direction of the axis C is referred to as image side. In the optical unit 1 illustrated in FIG. 1, the left side is the object side, and the right side is the image side. Moreover, a center axis of each portion may also be referred to as axis C. This is because the center axis of the portion coincides with the axis C at assembling.

The fixed portion 2 includes a fixed-portion main body 20, a front frame portion 4 that is attached to the object side of the fixed-portion main body 20, and that holds an object-side fixed-lens group Gf positioned on the object side relative to a movable lens group Gv held by the movable portion 3, a rear frame portion 5 that is attached to the image side of the fixed-portion main body 20, and that holds an image-side fixed-lens group Gb positioned on the image relative to the movable lens group, and a housing portion 6 that houses the fixed-portion main body 20, the movable portion 3, and the rear frame portion 5.

Figures 7, 8:
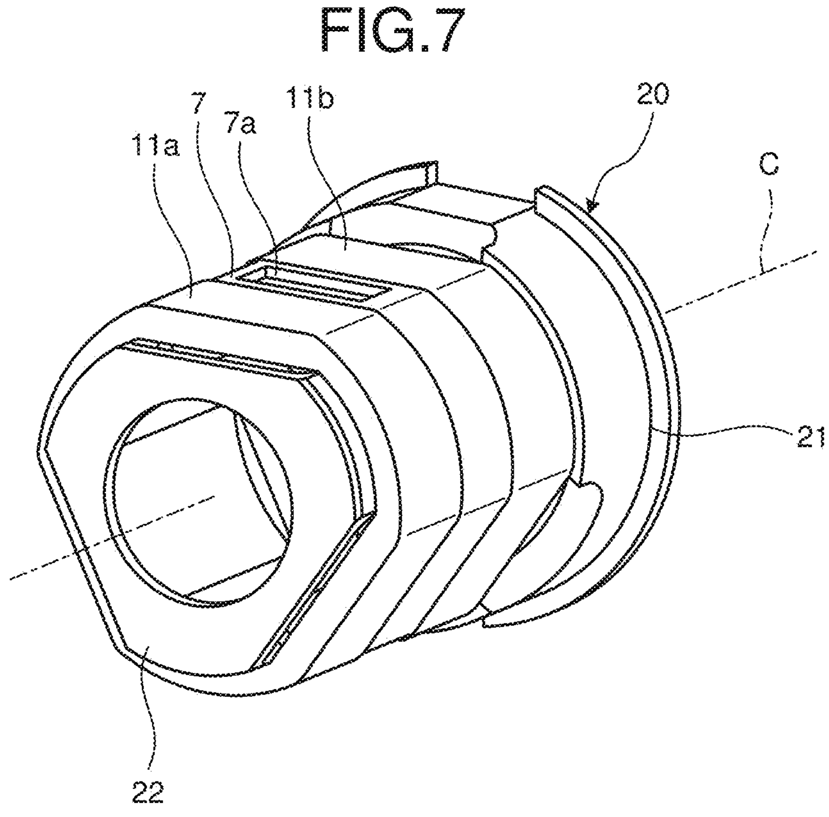
FIG. 7 is a perspective view (Part 1) illustrating a configuration of a fixed-portion main body of the optical unit according to the first embodiment of the disclosure.
FIG. 8 is an enlarged diagram of a part of the fixed-portion main body of the optical unit according to the first embodiment of the disclosure.
Figure 9:
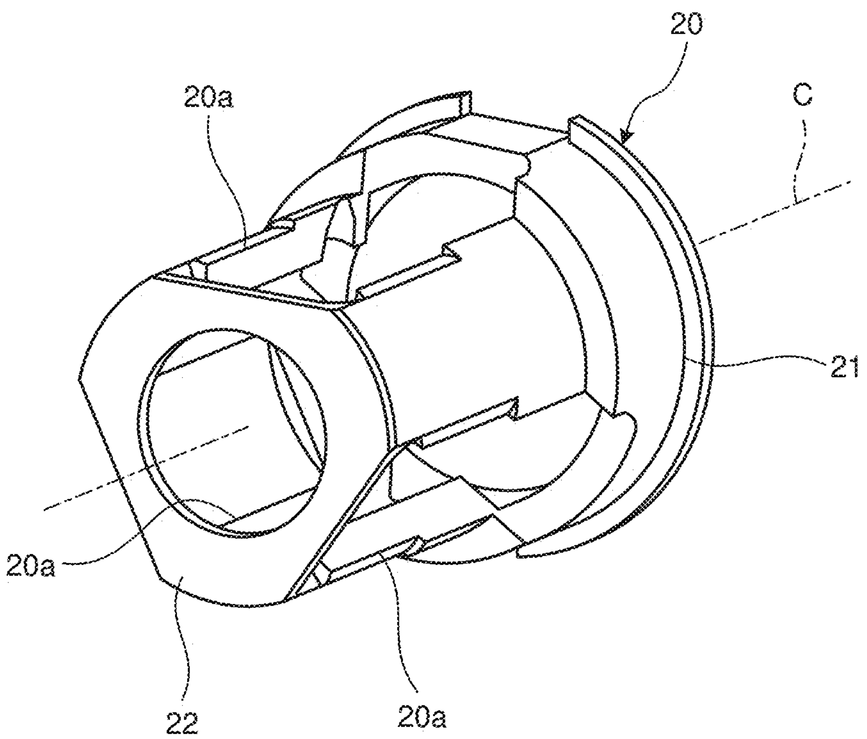
FIG. 9 is a perspective view (Part 2) illustrating the configuration of the fixed-portion main body of the optical unit according to the first embodiment of the disclosure.
Figure 10:
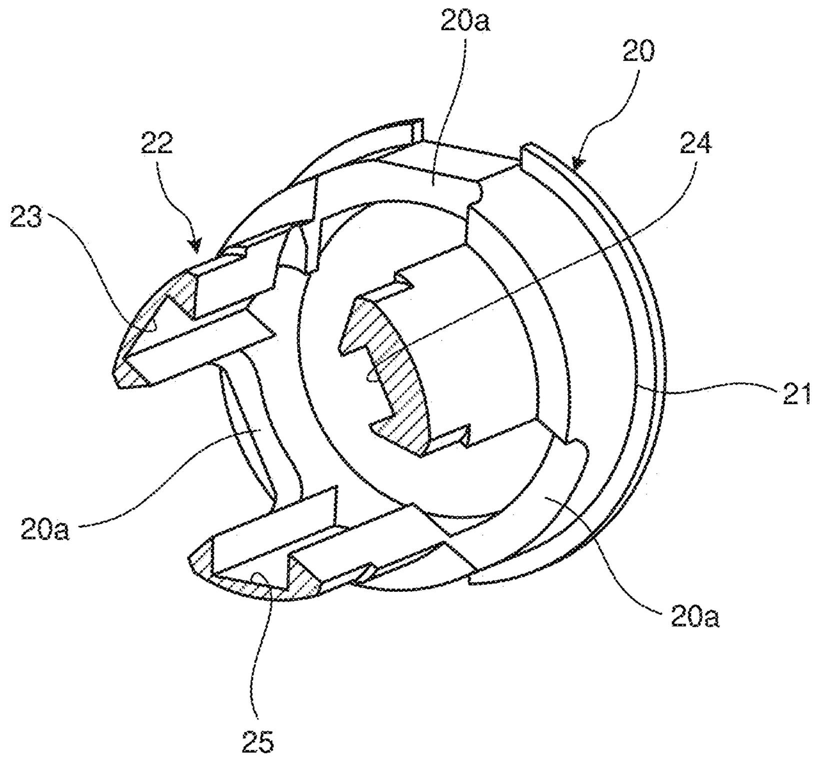
FIG. 10 is a perspective view illustrating a configuration of a part of the fixed-portion main body of the optical unit according to the first embodiment of the disclosure.

FIG. 7 is a perspective view illustrating a configuration of the fixed-portion main body of the optical unit according to the first embodiment of the disclosure. FIG. 8 is an enlarged diagram of a part of the fixed-portion main body of the optical unit according to the first embodiment of the disclosure. FIG. 9 is a perspective view illustrating a configuration of the fixed-portion main body of the optical unit according to the first embodiment of the disclosure. FIG. 10 is a perspective view illustrating a configuration of a part of the fixed-portion main body of the optical unit according to the first embodiment of the disclosure. The fixed-portion main body 20 is constituted of a cylindrical portion, and the axis C passes through the center of an interior of a cylinder. The fixed-portion main body 20 includes a first cylindrical portion 21 having the axis C as the center axis, and a second cylindrical portion 22 that extends in the direction of the axis C from one end of the first cylindrical portion 21.

The first cylindrical portion 21 has a stepped shape formed by protrusion of an end portion of an outer peripheral portion on the image side. A portion of the first cylindrical portion 21 is housed in the housing portion 6, and a stepped portion abuts on the housing portion 6.

The second cylindrical portion 22 has a cylindrical shape having an outer diameter that is smaller than an outer diameter of the first cylindrical portion 21. On a side surface of the second cylindrical portion 22, three through holes **20*a* that pierces through in a direction (radial direction) perpendicular to the axis C are formed (refer to FIG. 9). Moreover, on an inner peripheral surface of the second cylindrical portion 22, three rail portions (rail portions 23 to 25) that extend in the direction of the axis C are formed (refer to FIG. 10). Through holes 30*a* and the rail portions 23 to 25 are respectively formed at regular intervals of 120° along a circumferential direction on a cross-section in which a plane perpendicular to the axis C is the cutting plane. The through holes 30*a* and the rail portions 23 to 25 are arranged alternately in a circumferential direction of the second cylindrical portion 22. The rail portions 23 to 25 face the through holes 20*a*** with respect to the axis C.

Moreover, in a center portion in the direction of the axis C of the second cylindrical portion 22, a ring-shaped portion 7 that surrounds the outer periphery of the second cylindrical portion 22 is arranged (refer to FIG. 7). In a portion of the outer periphery of the ring-shaped portion 7, a housing groove **7*a* having a concave shape is formed. In the housing groove 7*a*, a detector 9 that outputs a detection signal to detect a position of the movable portion 3 is arranged. By arranging the detector 9 in the housing groove 7*a*, the detector 9 is positioned between a first coil 11*a* and a second coil 11*b* described later in the direction of the axis C. The detector 9 is connected to a substrate 9*a*. The substrate 9*a* is connected to a control substrate (not illustrated) that performs position detection. The detector 9 is constituted of, for example, a magnetic detector. The magnetic detector is implemented by using, for example, a Hall element and a magnetoresistive element (MR element). The magnetic detector is fixedly arranged, housed in the housing groove 7*a*. Based on a detection signal detected by the magnetic detector, a position of the movable portion 3 can be accurately detected. The detection signal is related to magnetism of a magnet 12**, and includes, for example, information indicating a magnetic field direction and a magnetic field intensity.

The front frame portion 4 holds the object-side fixed-lens group Gf. The object-side fixed-lens group Gf have multiple lenses (in this example, an object lens Lf1 and a lens Lf2) including the object lens Lf1 aligned in the direction of the axis C.

The rear frame portion 5 holds the image-side fixed-lens group Gb. The image-side fixed-lens group Gb have multiple lenses (lenses Lb1, Lb2) aligned in the direction of the axis C.

Figure 11:
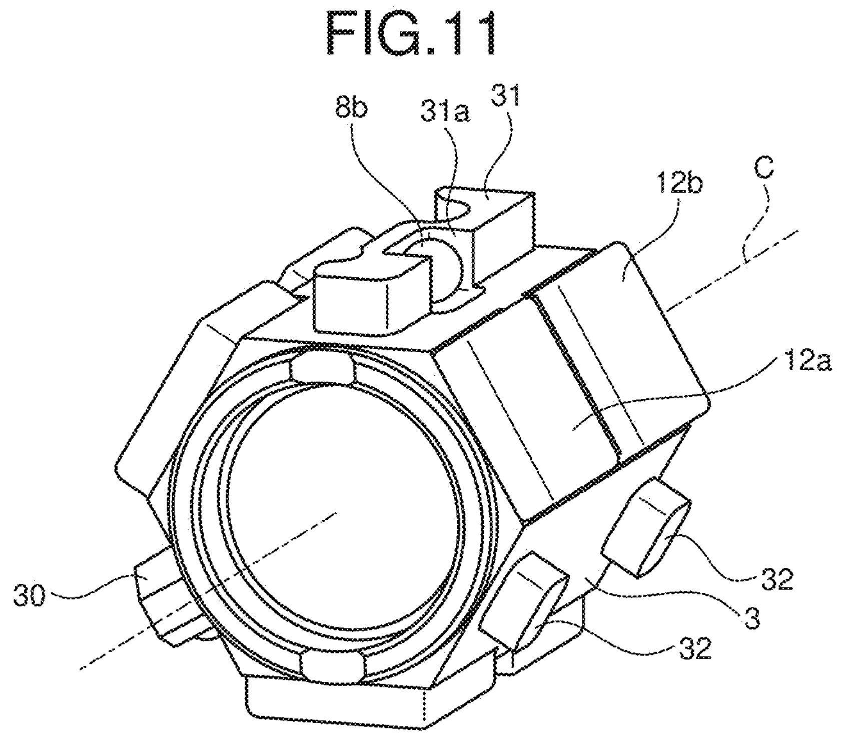
FIG. 11 is a perspective view (Part 1) illustrating a configuration of a movable portion of the optical unit according to the first embodiment of the disclosure.
Figure 12:
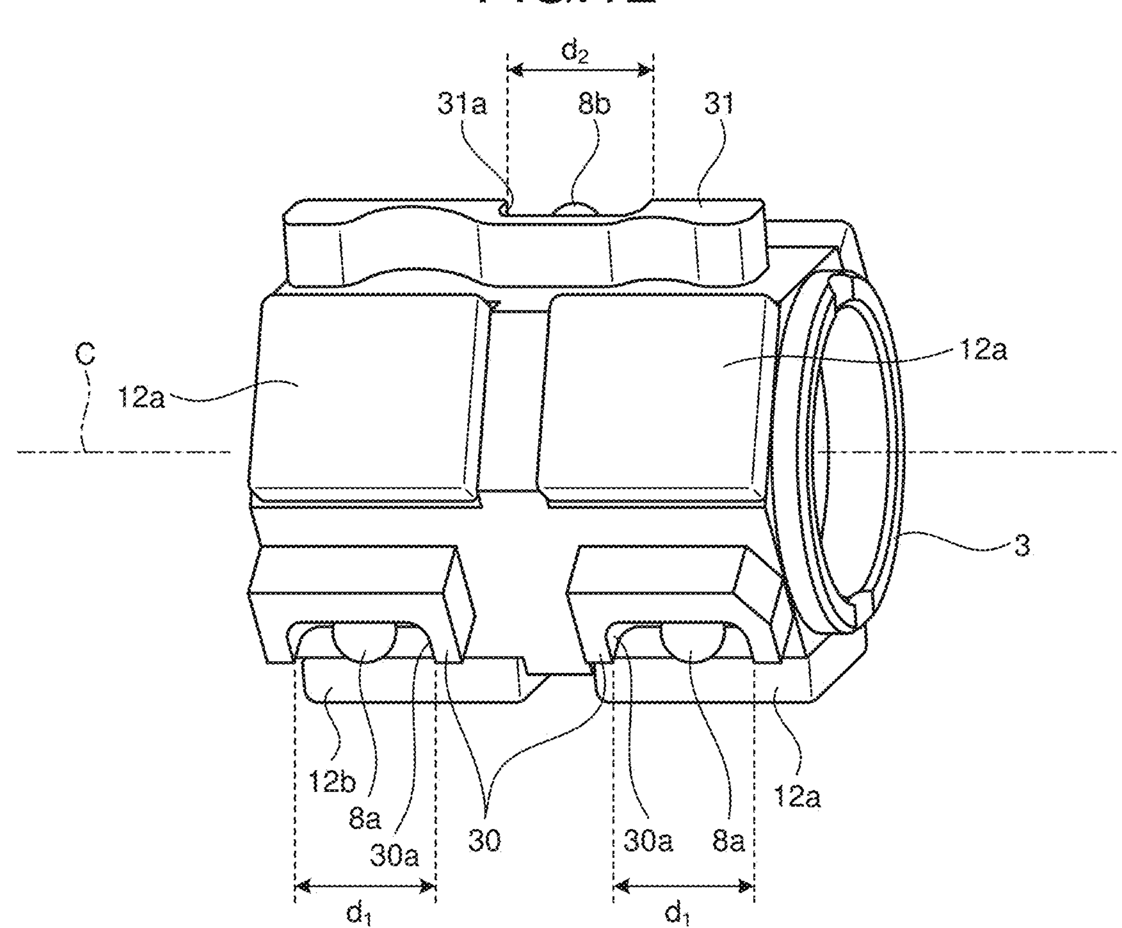
FIG. 12 is a perspective view (Part 2) illustrating the configuration of the movable portion of the optical unit according to the first embodiment of the disclosure.
Figure 13:
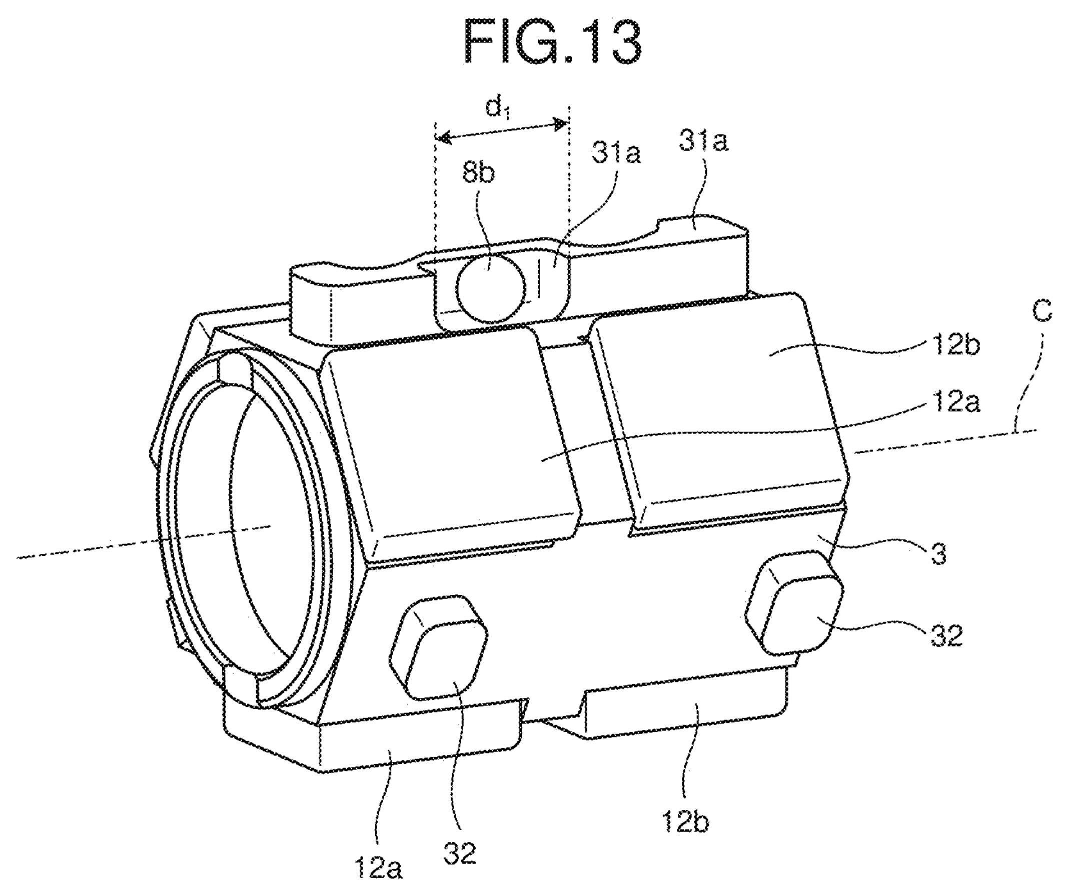
FIG. 13 is a perspective view (Part 3) illustrating the configuration of the movable portion of the optical unit according to the first embodiment of the disclosure.

FIG. 11 to FIG. 13 are perspective view illustrating a configuration of the movable portion of the optical unit according to the first embodiment of the disclosure. The movable portion 3 is constituted of a cylindrical portion with a hexagonal-shaped outer edge when viewed from the direction of the axis C. The movable portion 3 holds the movable lens group Gv. The movable lens group Gv is constituted of a single lens or multiple lenses (in this example, a lens Lv1) aligned in the direction of the axis C.

The movable portion 3 includes a first protruding portion 30, a second protruding portion 31, and a third protruding portion 32 that are arranged on an outer surface, and that protrude outward. The first protruding portion 30, the second protruding portion 31, and the third protruding portion 32 are respectively arranged on faces that are different from one another, and that are not adjacent to one another out of six faces constituting the outer surface of the movable portion 3. That is, the first protruding portion 30, the second protruding portion 31, and the third protruding portion 32 are arranged with gaps equivalent to one face of the hexagon constituting the outer surface of the movable portion 3.

The first protruding portion 30 is housed in the rail portion 23 when it is assembled in the optical unit 1. The first protruding portion 30 has a concave portion 30*a*. The concave portion 30*a* has a groove shape in which one end in a circumferential direction of the movable portion 3 is open. The first protruding portion 30 are provided by arranging two aligned in the direction of the axis C.

The second protruding portion 31 is housed in a rail portion 24 when it is assembled in the optical unit 1. The second protruding portion 31 has a concave portion 31*a*. The concave portion 31*a* has a groove shape in which one end in the circumferential direction of the movable portion 3 is open.

A distance $d_1$ in the direction of the axis C of the concave portion 30*a* is set to be equal to or larger than a moving distance of the movable portion 3.

Moreover, a distance $d_2$ in the direction of the axis C of the concave portion 31*a* is set to be equal to or larger than the moving distance of the movable portion 3.

The distance $d_1$ and the distance $d_2$ may be identical to each other, or may be different distances from each other as long as they are set to be equal to or larger than the moving distance.

The third protruding portion 32 has a pillar shape that extends in a direction perpendicular to the axis C.

Figure 14:
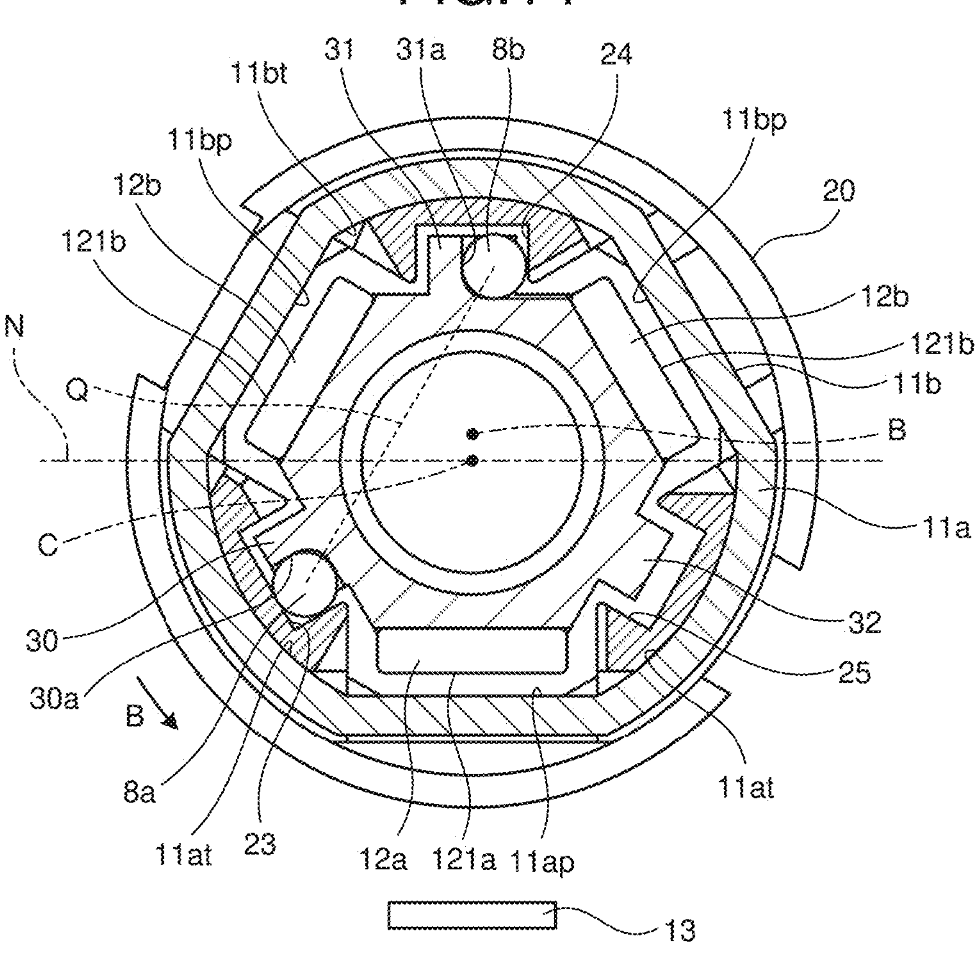
FIG. 14 is a cross-section of the optical unit according to the first embodiment of the disclosure.

FIG. 14 is a cross-section of the optical unit according to the first embodiment of the disclosure. FIG. 14 illustrates cross-sections on different cutting planes with an axis N perpendicular to the axis C as their boundary.

Between each of the concave portions 30*a* and the rail portion 23, a first ball 8*a* is present. The first ball 8*a* that is housed in one of the concave portion 30*a* corresponds to a first slider, and the first ball 8*a* that is housed in the other concave portion 30*a* corresponds to a third slider.

Moreover, between the concave portion 31*a* and the rail portion 24, a second ball 8*b* is present. The second ball 8*b* housed in the concave portion 31*a* corresponding to a second slider.

In a state in which the movable portion 3 is housed in the fixed-portion main body 20, the respective first balls 8*a* are sandwiched between the second cylindrical portion 22 and the rail portion 23. In this case, one of the first ball 8*a* abuts on a wall surface of the rail portion 23, and the other one of the first ball 8*a* also abuts on a side wall of the rail portion 23.

The third protruding portion 32 is positioned in the rail portion 25 in a state in which the movable portion 3 is housed in the fixed-portion main body 20.

Subsequently, a configuration of the voice coil motor 10 will be explained. The voice coil motor 10 includes a coil 11 that is arranged in the fixed-portion main body 20 of the fixed portion 2, and a magnet 12 that is arranged in the movable portion 3 facing the coil 11 (for example, refer to FIG. 2, FIG. 3, and FIG. 14). The voice coil motor 10 functions as a driver.

The coil 11 includes a first coil 11*a* that is wound around an outer periphery of the second cylindrical portion 22 of the fixed-portion main body 20, and a second coil 11*b* that is aligned in the direction of the axis C of the first coil 11*a*, and that is wound on an outer periphery of the second cylindrical portion 22 of the fixed-portion main body 20 (for example, refer to FIG. 7). Between the first coil 11*a* and the second coil 11*b*, the ring-shaped portion 7 is arranged. The coils 11 may be provided by arranging pre-wound ones later. The first coil 11*a* and the second coil 11*b* adjacent to each other in the direction of the axis C are preferable to be electrically connected in series, but may be connected in parallel.

The first coil 11*a* and the second coil 11*b* include flat surface portions 11*ap* and 11*bp*, respectively, that face the through holes 20*a* of the fixed-portion main body 20. Moreover, the first coil 11*a* and the second coil 11*b* include cylindrical portions 11*at* and 11*bt*, respectively, that face the second cylindrical portion 22. the first coil 11*a* has a form in which the three flat surface portions 11*ap* and the three cylindrical portions 11*bt* are arranged alternately on a cross-section perpendicular to the axis C. Similarly, the second coil 11*b* has a form in which the three flat surface portions 11*bp* and the three cylindrical portions 11*bt* are arranged alternately on a cross-section perpendicular to the axis C.

The magnet 12 faces the respective flat surface portions 11*ap* and 11*bp* inside the flat surface portion 11*ap* of the first coil 11*a* and the flat surface portion 11*bp* of the second coil 11*b*, and includes three flat-shaped first magnets 12*a* and three flat-shaped second magnets 12*b* that are aligned in the direction of the axis C. The three sets of the first magnet 12*a* and the second magnet 12*b* are arranged at regular intervals of 120° along a circumferential direction on a cross-section having a plane perpendicular to the axis C as a cutting surface. By arranging the respective sets of magnets at regular intervals, the first magnets 12*a* and the second magnets 12*b* can be arranged stably. This enables to form a stable magnetic field in the voice coil motor 10, and to suppress wobbling of the movable portion 3 that moves relative to the fixed portion 2. Although the magnets 12 are arranged around the axis C at intervals of 120° each in the first embodiment, the magnets 12 may be arranged at different angular intervals.

A total of widths of the first magnet 12*a* and the second magnet 12*b* in the direction of the axis C is preferable to be shorter than a total of widths of the first coil 11*a* and the second coil 11*b* in the direction of the axis C. By satisfying this condition, within a moving range of the movable portion 3, it is possible to make the first magnet 12*a* and the second magnet 12*b* always be present within a width of the first coil 11*a* and the second coil 11*b* in the direction of the axis C.

Figure 15:
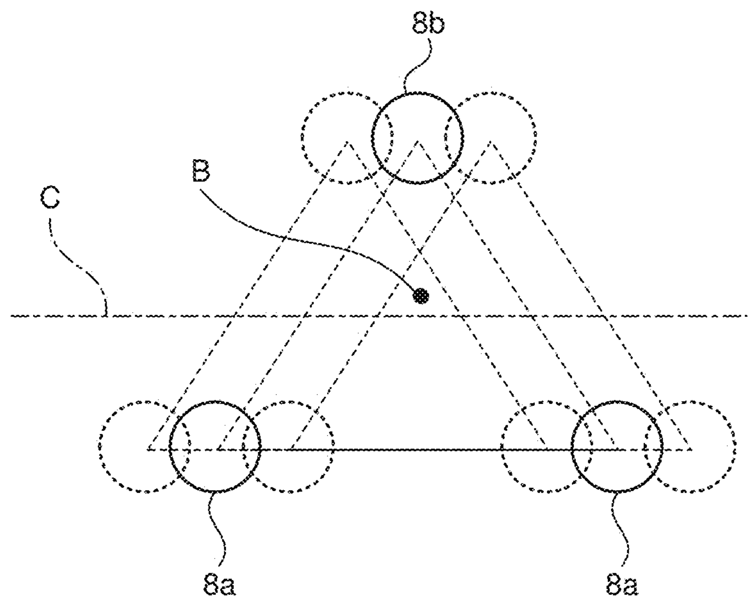
FIG. 15 is a diagram explaining movement of each ball and the center of gravity of the movable portion.

FIG. 15 is a diagram explaining about movement of each ball and a center of gravity of the movable portion. FIG. 15 illustrates an example of arrangement of the respective balls when viewed from a direction perpendicular (for example, a direction toward the axis C from an upper left portion in FIG. 14) to the axis C and a line segment (for example, line Q in FIG. 14) connecting the center of gravity of the first ball 8*a* and the center of gravity of the second ball 8*b*, and an arrangement of each ball after movement of the movable portion 3. FIG. 15 illustrates a ball (solid line) positioned in the center of a moving range of the movable portion 3 and a ball (broken line) at positions when the movable portion 3 has moved to the image side and the object side from a central portion. The two first balls 8*a* and the second ball 8*b* are arranged at positions such that the center B of gravity of the movable portion 3 is located inside a triangle regardless of a position of the movable portion 3, in the triangle formed by connecting the centers of gravities of the respective first balls 8*a* and the center of gravity of the second ball 8*b*.

Figure 16:
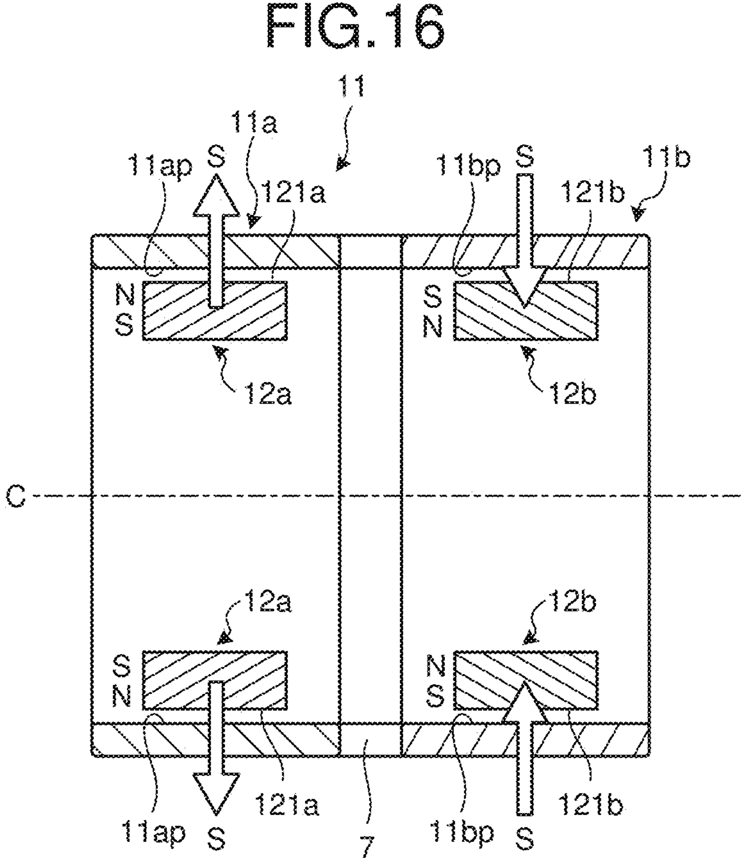
FIG. 16 is a diagram illustrating a configuration of a voice coil motor on a cross-section cut on a plane that passes through an axis C and that is parallel to the axis C.

FIG. 16 is a diagram illustrating a configuration of only the voice coil motor on a cross-section that passes through the axis C and that is cut on a plane parallel to the axis C as a cutting plane. FIG. 16 illustrates different cutting planes with the axis C as their boundary. The first magnet 12*a* and the second magnet 12*b* that are paired in the direction of the axis C are arranged to be separated from each other. The set of the first magnets 12*a* and the set of the second magnets 12*b* are respectively magnetized in a radial direction, and have magnetic poles opposite to each other. In the case illustrated in FIG. 16, the first magnet 12*a* has its N pole on a side closer to the first coil 11*a*, and its S pole on the opposite side, and the second magnet 12*b* has its S pole on a side closer to the second coil 11*b* and its N pole on the opposite side. In this case, a direction of magnetic polarization of the first magnet 12*a* and the second magnet 12*b* is perpendicular to the axis C (refer to a white arrow S indicated in FIG. 16). More generally speaking, the direction of magnetic polarization of the first magnet 12*a* and the second magnet 12*b* can be any direction as long as it intersects the axis C.

In the first embodiment, the coil 11 is preferable to be wound such that a winding direction reverse between the set of the first magnets 12*a* and the set of the second magnets 12*b*. For example, when the first coil 11*a* is wound in a direction of an arrow B, the second coil 11*b* may be wound in the opposite direction. Alternatively, the first coil 11*a* and the second coil 11*b* may be connected by winding the first coil 11*a* and the second coil 11*b* in an identical direction, and by reversing the direction of the electric current. In this case, when an electric current is flowed in a direction of an arrow B indicated in FIG. 11 to the first coil 11*a*, the electric current is to be flowed in the opposite direction to the second coil 11*b*.

Moreover, in an outer portion of the housing portion 6, a housing groove 6*a* is formed. In the housing groove 6*a*, a magnetic material 13, which is a biasing part, is arranged. The magnetic material 13 attracts the magnet 12 by magnetic force, and thereby brings the movable portion 3 toward the fixed-portion main body 20. The biasing material is not limited thereto, and may be any material as long as it is capable of attracting the movable portion 3 toward the fixed-portion main body 20. For example, it may be a metal, such as iron. Furthermore, the biasing part may be configured to attract the movable portion 3 toward the fixed-portion main body 20 by applying force in a direction of separating the magnet 12 from the biasing part.

In a state in which the movable portion 3 is housed in the fixed-portion main body 20, the movable portion 3 and the fixed-portion main body 20 are not in direct contact with each other, and a relative positional relationship viewed from the direction of the axis C is such that positions of the movable portion 3 and the fixed-portion main body 20 are fixed through the two first balls 8*a* and the second ball 8*b*.

Figure 17:
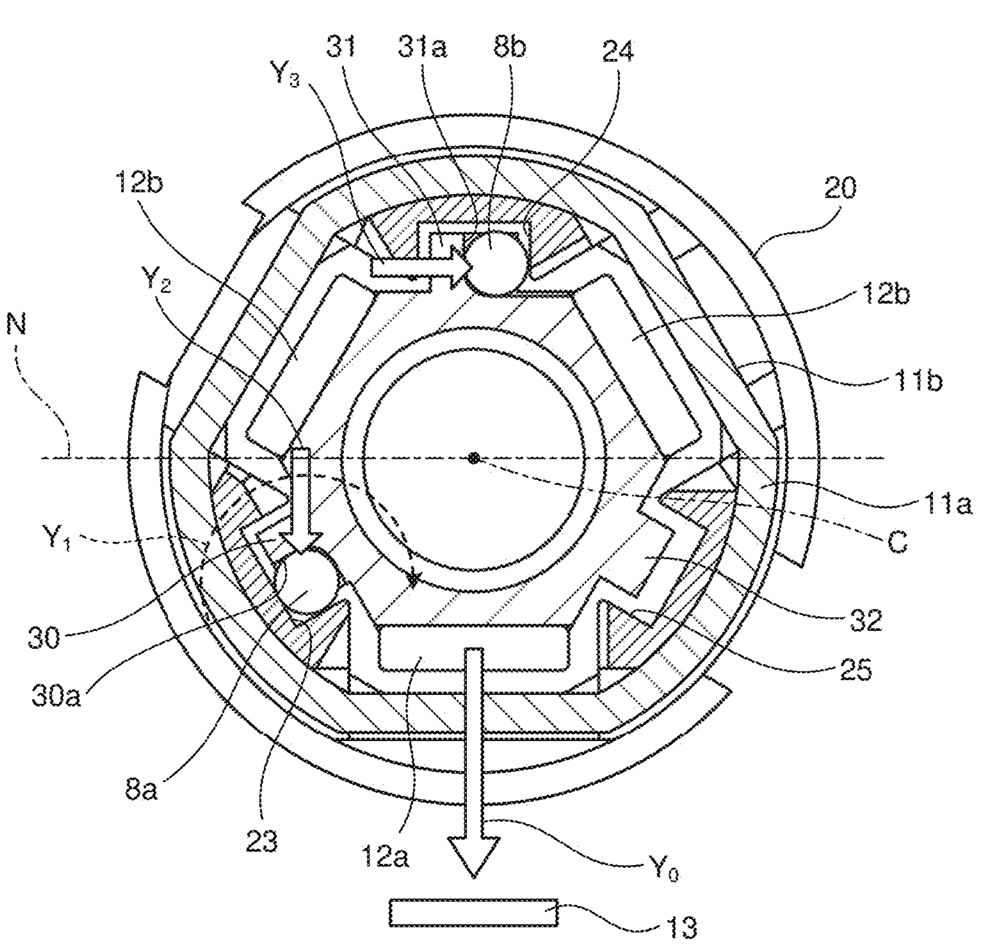
FIG. 17 is a diagram for explaining a load applied on the optical unit according to the first embodiment of the disclosure.

FIG. 17 is a diagram for explaining a load on the optical unit according to the first embodiment of the disclosure. FIG. 17 illustrates cross-sections having different cutting planes with the axis N perpendicular to the axis C as their boundary, similarly to FIG. 14. In the optical unit 1, the magnet 12 (the first magnet 12*a* in FIG. 17) receives a biasing force $Y_0$ by magnetic force of the magnetic material 13, to be attracted toward the magnetic material 13. By this attraction, a rotational moment $Y_1$ around the first ball 8*a* is applied to the movable portion 3. At this time, to the movable portion 3, a pressing force $Y_2$ with which the first protruding portion 30 pushes the first ball 8*a* toward the rail portion 23 is applied by the biasing force $Y_0$, and a pressing force $Y_3$ with which the second protruding portion 31 pushes the second ball 8*b* toward the rail portion 24 is also applied by the rotational moment $Y_1$.

Figure 18:
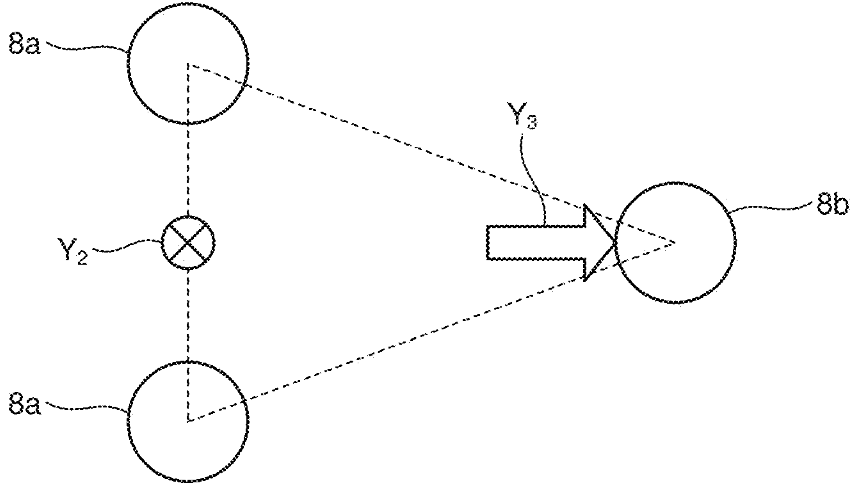
FIG. 18 is a diagram for explaining a positional relationship between each ball and a biasing force.

FIG. 18 is a diagram for explaining a positional relationship between each ball and the biasing force. FIG. 18 is a diagram illustrating an example of a positional relationship among the two first balls 8*a* and the second ball 8*b* projected on a plane parallel to the axis N and passing through the axis C in the direction of $Y_0$. In the triangle formed by connecting the centers of gravities of the first balls 8*a* and the center of gravity of the second ball 8*b* (broken line in FIG. 18), only a component orthogonal to the biasing force $Y_0$ (only the pressing force $Y_3$) is applied to the second ball 8*b*. Therefore, the biasing force $Y_0$ is to be applied to the respective first balls 8*a* from a position on a line segment (broken line) between the first balls 8*a*. A component ratio of the biasing force $Y_0$ applied to the respective first balls 8*a* varies according to a relative position (position of the movable portion 3) of the respective balls 8*a*. By positioning a point of action of the biasing force $Y_0$ at a central position in the direction of the axis C relative to the position of the respective first balls 8*a*, it is possible to make the component ratio of the biasing force $Y_0$ applied to the respective first balls 8*a* uniform. By this application of the pressing force $Y_2$, a component in a direction of the pressing force $Y_2$ out of the biasing force $Y_0$ from the magnetic material 13 is utilized effectively, and it is possible to stabilize the position of the movable portion 3 relative to the fixed-portion main body 20.

In the optical unit 1 having the configuration described above, the movable portion 3 in which the first magnet 12*a* is arranged facing the first coil 11*a* inside in the radial direction of the fixed-portion main body 20 wound on the first coil 11*a* is provided. Therefore, the flat surface portion 11*ap* of the first coil 11*a* is present in a magnetic field in a direction orthogonal to a plane 121*a* (refer to FIG. 16) outside in the radial direction of the respective first magnets 12*a*. The second magnet 12*b* is also configured similarly. Therefore, the driving efficiency is improved, and it becomes possible to move the movable portion 3 swiftly. Moreover, by forming the surface 121*a* outside in the radial direction of the first magnet 12*a* and the surface 121*b* outside in the radial direction of the second magnet 12*b* into flat surfaces, assembly of the optical unit 1 becomes easy.

Furthermore, when an electric current is flowed through the coil 11 of the optical unit 1, a force in the direction of the axis C is generated in the movable portion 3 by an influence of a magnetic field of the magnet 12, and the movable portion 3 moves in the direction of the axis C relative to the fixed portion 2. For example, by controlling the respective electric currents to be flowed through the first coil 11 and the second coil 11*b*, it is possible to move the movable portion 3 relative to the fixed portion 2. In this case, the first ball 8*a* and the second ball 8*b* slide (in this example, rotate) in synchronization with the movement of the movable portion 3. By rotation of the first ball 8*a* and the second ball 8*b*, friction between the fixed-portion main body 20 and the movable portion 3 is reduced. Even in a state in which the movable portion 3 moves relative to the fixed portion 2, a surface outside in the radial direction of the magnet 12 is arranged in the through hole 20*a* of the fixed-portion main body 20.

Figure 19:
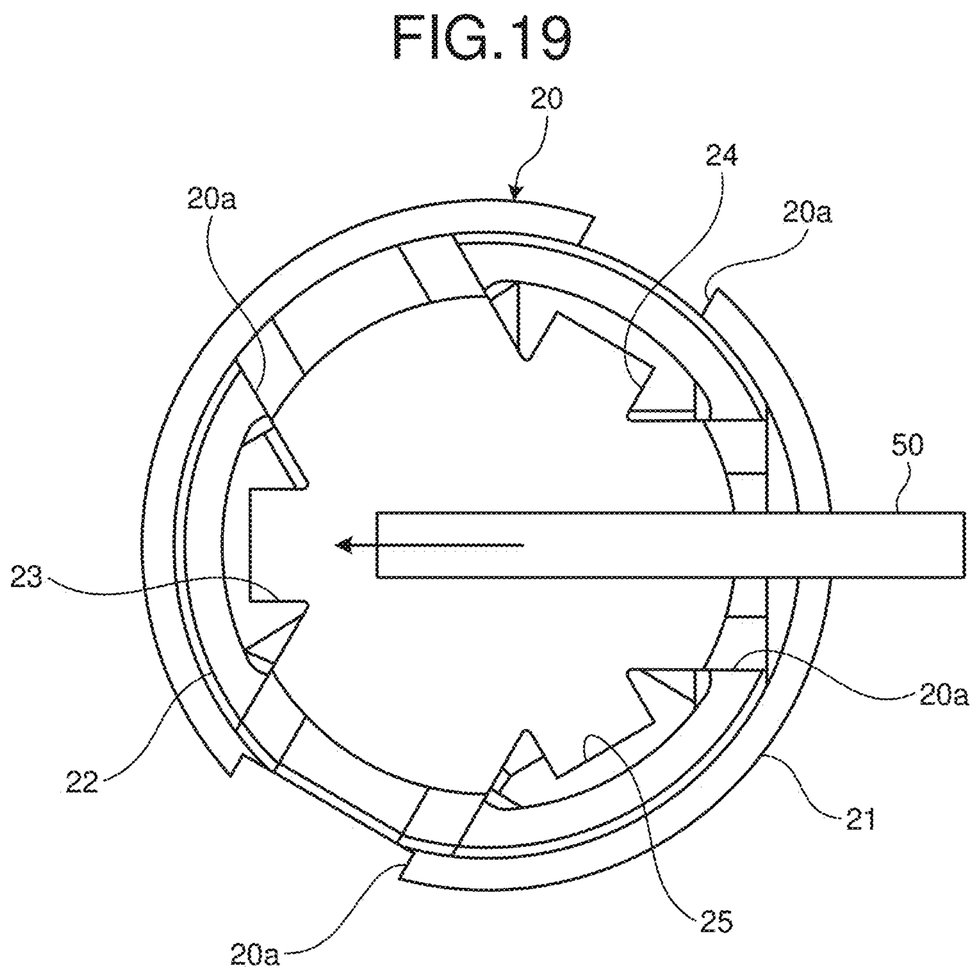
FIG. 19 is a diagram for explaining manufacturing of the fixed-portion main body of the optical unit according to the first embodiment of the disclosure.

Manufacturing of the fixed-portion main body 20 will be explained, referring to FIG. 19. FIG. 19 is a diagram for explaining about the manufacturing of the fixed-portion main body of the optical unit according to the first embodiment of the disclosure. In the fixed-portion main body 20, for example, the rail portions 23 to 25 are formed by a cutter 50. In the fixed-portion main body 20, the rail portions 23 to 25 are formed to face the through holes 20*a*, respectively. Accordingly, by inserting the cutter 50 into the through holes 20*a* to form the rail portions 23 to 25, the rail portions 23 to 25 can be formed easily.

According to the first embodiment explained above, by arranging the first balls 8*a* and the second ball 8*b* between the fixed portion 2 and the movable portion 3, and by moving the movable portion 3 relative to the fixed portion 2 by rotation of the balls, the movable portion 3 (movable lens) can be moved smoothly relative to the fixed portion 2.

Moreover, according to the first embodiment, because the detector 9 is positioned between the first coil 11*a* and the second coil 11*b* in the direction of the axis C, an influence of leakage magnetic field of the coil 11 can be reduced, and reduction in detection accuracy caused by the leakage magnetic field can be suppressed. Particularly, when the detector 9 and the magnets 12 (the first magnets 12*a* or the second magnets 12*b*) are separated by movement of the movable portion 3, the influence of the leakage magnetic field becomes large, but in the first embodiment, the detector 9 is positioned in such a manner that it is less susceptible to the influence of the leakage magnetic field and, therefore, the detection accuracy can be ensured. Moreover, by arranging the detector 9 between the coils, it is possible to downsized compared to a case in which the detector 9 is positioned outward in the radial direction of the coil 11.

Furthermore, according to the first embodiment, by configuring the fixed portion 2 by using the fixed-portion main body 20, the front frame portion 4, and the rear frame portion 5, it is possible to reduce the number of parts and assembly processes, and to increase flexibility in design, thereby enabling cost reduction to be achieved.

Moreover, according to the first embodiment, because the coil 11 is wound about the axis C, it is possible to make the sliding axis of the movable portion 3 and the axis of action of a propulsive force generated by the voice coil motor 10 the same, thereby enabling stable driving.

Furthermore, according to the first embodiment, the magnets 12 are arranged in plurality in a symmetric manner with respect to the axis C. Therefore, it is possible to increase the driving force stably.

Moreover, according to the first embodiment, the magnet 12 includes multiple sets of the first magnet 12*a* and the second magnet 12*b* that are adjacent to each other along the direction of the axis C, and that have the opposite directions of magnetic polarization, the first magnets 12*a* have the identical direction of magnetic polarization, the coil 11 includes the first coil 11*a* facing the first magnets 12*a*, and the second coil 11*b* that faces the second magnets 12*b* and that is connected to the first coil 11*a*, and the directions in which an electric current flows in the first coil 11*a* and the second coil 11*b* are reverse and, therefore, the driving force can be increased.

Second Embodiment

Figure 20:
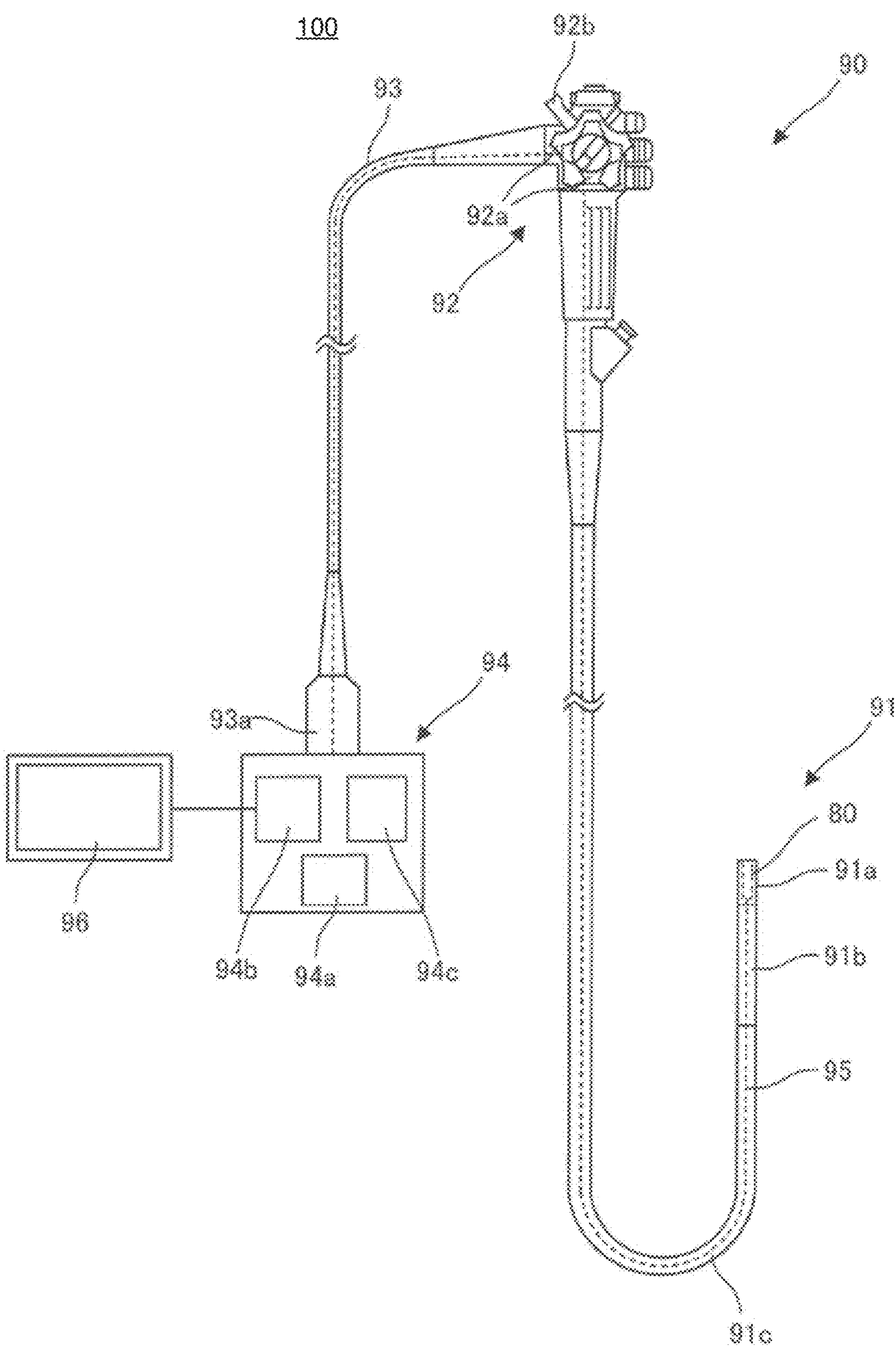
FIG. 20 is a diagram illustrating a configuration of an endoscope system that includes an endoscope according to a second embodiment of the disclosure.

FIG. 20 is a diagram illustrating a configuration of an endoscope system that includes an endoscope according to a second embodiment of the disclosure. An endoscope system 100 illustrated in the drawing includes an endoscope 90, a control device 94, and a display device 96. The endoscope 90 includes the optical unit 1 described above. In the second embodiment, it will be explained assuming that, for example, the optical unit 1 according to the first embodiment is equipped.

The endoscope 90 can be introduced inside a body of a subject, such as human body, and optically images a predetermined observation part in the subject. The subject to which the endoscope 90 is introduced is not limited to a human body, and may also be other living bodies, or may be an artificial object, such as a machine and a building structure. In other words, the endoscope 90 may be a medical endoscope or an industrial endoscope.

The endoscope 90 includes an insertion portion 91 configured to be inserted into the inside of a subject, an operating portion 92 that is positioned at a proximal end of the insertion portion 91, and a universal cord 93 as a composite cable that extends from the operating portion 92.

The insertion portion 91 includes a distal end portion 91*a* arranged at a distal end, a bendable portion 91*b* that is bendable and arranged on a proximal end side of the distal end portion 91*a*, and a flexible tubular portion 91*c* that is arranged on a proximal end side of the bendable portion 91*b*, connected to a distal end side of the operating portion 92, and has flexibility. In the distal end portion 91*a*, an imaging portion 80 that gathers light from a subject to image the subject is arranged. The imaging portion 80 includes the optical unit 1 that gathers light from the subject, and an imager that subjects the light gathered by the optical unit 1 to photoelectric conversion, to output. The imager is constituted of a charge coupled device (CCD) or a complementary metal oxide semiconductor (CMOS). The endoscope 90 may be a rigid endoscope that does not include the flexible tubular portion 91*c* in the insertion portion 91.

The operating portion 92 includes an angle operating portion 92*a* that operates a bending state of the bendable portion 91*b*, and a zoom operating portion 92*b* that instructs the operation of the voice coil motor 10 described above, and performs zooming operation in the optical unit 1. The angle operating portion 92*a* is formed in a knob form, and the zoom operating portion 92*b* is formed in a lever form, but the respective parts may take other forms, such as a volume switch and a push switch.

The universal cord 93 is a part that connects the operating portion 92 and the control device 94. The endoscope 90 is connected to the control device 94 through a connector 93*a* arranged at a proximal end portion of the universal cord 93.

To the insertion portion 91, the operating portion 92, and the universal cord 93, a cable 95, such as a wire, an electric line, and a fiber, is inserted through.

The control device 94 includes a drive controller 94*a* that controls a bending state of the bendable portion 91*b*, an image controller 94*b* that controls the imaging portion 80, and a light-source controller 94*c* that controls a light source device not illustrated. The control device 94 includes a processor, such as a central processing unit (CPU), and comprehensively controls the entire endoscope system 100.

The drive controller 94*a* includes an actuator, and is mechanically connected to the operating portion 92 and the bendable portion 91*b* through a wire. The drive controller 94*a* controls a bending state of the bendable portion 91*b* by moving the wire back and forth.

The image controller 94*b* is electrically connected to the imaging portion 80 and the operating portion 92 through the electric line. The image controller 94*b* performs the drive control of the voice coil motor 10 included in the imaging portion 80, and processing of an image that captured by the imaging portion 80. The image processed by the image controller 94*b* is displayed on the display device 96.

The light-source controller 94*c* is optically connected to the light source and the operating portion 92 through an optical fiber. The light-source controller 94*c* controls brightness of light of the light source irradiated from the distal end portion 91*a*.

The operating portion 92 may be formed separately from the insertion portion 91, to be configured to operate the insertion portion 91 by remote control.

The endoscope system 100 having the configuration as described above has the imaging portion 80 equipped with the optical unit 1 described above. Therefore, it is compact, and is capable of changing zoom levels quickly, and is suitable for capturing moving images.

Moreover, according to the endoscope system 100, because the coil 11 is arranged in the fixed portion 2 while the magnet 12 is arranged in the movable portion 3, it is not necessary to move a cable connected to the coil 11. Therefore, there is no risk of disconnection caused by the cable moving in limited space in the distal end portion 91*a* of the endoscope 90, leading to improved durability.

Other Embodiments

The embodiments to implement the disclosure have so far been explained, but the disclosure is not to be limited to the embodiments described above. For example, the number of magnets arranged in the movable portion 3 is not limited to three sets as described in the first embodiment, and it may be one set, or multiple sets, such as two sets and four sets to be arranged.

Furthermore, although an example in which three balls (the two first balls 8*a* and the second ball 8*b*) are included as the sliders that slide in synchronization with movement of the movable portion 3 has been explained, it is applicable if at least two balls are arranged as the slider, as long as they are positioned between the fixed-portion main body 20 and the movable portion 3, and enable smooth movement of the movable portion 3. Furthermore, other than balls, any object that enables smooth movement of the movable portion 3 in synchronization with the movement of the movable portion 3, such as a roller and a caterpillar, can be adopted.

Moreover, the through hole 20*a* arranged in the fixed-portion main body 20 is only required to enable assembly of the magnet 12, and it may be formed not piercing through to the outer peripheral side in the radial direction.

Furthermore, in the optical unit 1, arrangement of the coil 11 and the magnet 12 may be reversed. That is, the coil 11 may be arranged in the movable portion 3, and the magnet 12 may be arranged in the fixed portion 2.

As explained above, the optical unit and the endoscope according to the disclosure are useful for moving the movable portion smoothly relative to the fixed portion.

According to the disclosure, an effect that a movable portion can be smoothly moved relative to a fixed portion can be produced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical unit comprising:
a fixed portion having a cylindrical shape;
a movable portion holding a lens, the movable portion being arranged movably inside the fixed portion;
a first slider that is arranged between the fixed portion and the movable portion, the first slider being configured to slide with a movement of the movable portion;
a second slider that is arranged between the fixed portion and the movable portion, and at a position different from a position of the first slider, the second slider being configured to slide with the movement of the movable portion;
a driver that includes a coil and a magnet, the driver being configured to move the movable portion in a direction of an optical axis of the lens relative to the fixed portion; and
a biasing part that is arranged outside the movable portion, the biasing part being configured to cause the magnet to generate a biasing force to push the movable portion toward the fixed portion, wherein
the fixed portion includes a first rail portion and a second rail portion guiding a movement of the first slider and the second slider, respectively, and extending in a direction of the optical axis,
the biasing part is arranged at a position facing the second rail portion through the optical axis of the lens,
the first slider abuts on the first rail portion, and is pushed in a direction horizontal to the biasing force, and
the second slider abuts on the second rail portion, and is pushed in a direction perpendicular to the biasing force.

2. The optical unit according to claim 1, wherein
the first slider is arrange in the movable portion at a position at which a rotational moment is generated around the first slider.

3. The optical unit according to claim 1, further comprising
a third slider that is aligned in an optical axis direction of the optical unit relative to the first slider and that is present between the fixed portion and the movable portion, the third slider being configured to slide with the movement of the movable portion.

4. The optical unit according to claim 2, wherein
the first slider, the second slider, and the third slider are arranged at positions at which a center of gravity of the movable portion is located within a triangle formed by connecting centers of gravity of the respective sliders, and a pressing force of a component perpendicular to the biasing force is applied to the second slider.

5. The optical unit according to claim 1, wherein
the fixed portion includes a third rail portion extending in the direction of the optical axis, and the first rail portion, the second rail portion, and the third rail portion are arranged at regular intervals along a circumferential direction of the fixed portion.

6. The optical unit according to claim 5, wherein
the movable portion has a hexagonal shape,
includes a first protruding portion, a second protruding portion, and a third protruding portion that are arranged on an outer surface of the movable portion, and
the first protruding portion, the second protruding portion, and the third protruding portion are arranged on surfaces different from one another, and are not adjacent to one another.

7. The optical unit according to claim 6, wherein the first protruding portion, the second protruding portion, and the third protruding portion are housed in the first rail portion, the second rail portion, and the third rail portion, respectively.

8. The optical unit according to claim 7, wherein the first protruding portion includes a first concave portion having a groove shape in which one end in a circumferential direction of the movable portion is open, and a third concave portion aligned with the first concave portion in the direction of the optical axis, the second protruding portion includes a second concave portion having a groove shape in which one end in the circumferential direction of the movable portion is open, and the first slider, the second slider, and the third slider are arranged in the first concave portion, the second concave portion, and the third concave portion, respectively.

9. The optical unit according to claim 1, wherein the first slider, the second slider, and the third slider are arranged such that each side of a triangle formed by connecting centers of gravity of the respective sliders is uniform.

10. The optical unit according to claim 1, wherein the magnet includes three sets of a first magnet and a second magnet that are arranged on different outer surfaces from one another of the movable portion, and the first magnet and the second magnet are respectively magnetized in a radial direction of the movable portion, magnetic polarizations of the first magnet and the second magnet are reversed to each other, and the three sets of the first magnet and the second magnet are arranged at regular intervals along a circumferential direction of the movable portion.

11. The optical unit according to claim 1, wherein in the fixed portion, a through hole in which a part of the magnet is housed is formed at a position facing the first rail portion and the second rail portion through a center axis of the fixed portion.

12. The optical unit according to claim 1, wherein the driver includes a plurality of coils aligned in an optical axis direction of the optical unit, and includes a detector that is arranged between the coils, the detector being configured to output a detection signal to detect a position of the movable portion.

13. An endoscope configured to be inserted into an inside of a subject to observe the inside of the subject, the endoscope comprising:

an optical unit;

an imager configured to convert light guided by the optical unit into an electrical signal; and a controller configured to control driving of the optical unit, wherein the optical unit includes:

a fixed portion having a cylindrical shape;

a movable portion holding a lens, the movable portion being arranged movably inside the fixed portion;

a first slider that is arranged between the fixed portion and the movable portion, the first slider being configured to slide with a movement of the movable portion;

a second slider that is arranged between the fixed portion and the movable portion, and at a position different from a position of the first slider, the second slider being configured to slide with the movement of the movable portion;

a driver that includes a coil and a magnet, the driver being configured to move the movable portion in a direction of an optical axis of the lens relative to the fixed portion; and a biasing part that is arranged outside the movable portion, the biasing part being configured to cause the magnet to generate a biasing force to push the movable portion toward the fixed portion, wherein the fixed portion includes a first rail portion and a second rail portion guiding a movement of the first slider and the second slider, respectively, and extending in a direction of the optical axis, the biasing part is arranged at a position facing the second rail portion through the optical axis of the lens, the first slider abuts on the first rail portion, and is pushed in a direction horizontal to the biasing force, and the second slider abuts on the second rail portion, and is pushed in a direction perpendicular to the biasing force.

14. The endoscope according to claim 13, wherein the first slider is arrange in the movable portion at a position at which a rotational moment is generated around the first slider.

15. The endoscope according to claim 13, further comprising a third slider that is aligned in an optical axis direction of the optical unit relative to the first slider and that is present between the fixed portion and the movable portion, the third slider being configured to slide with the movement of the movable portion.

16. The endoscope according to claim 14, wherein the first slider, the second slider, and the third slider are arranged at positions at which a center of gravity of the movable portion is located within a triangle formed by connecting centers of gravity of the respective sliders.

17. The endoscope according to claim 13, wherein the fixed portion includes a third rail portion extending in the direction of the optical axis, and the first rail portion, the second rail portion, and the third rail portion are arranged at regular intervals along a circumferential direction of the fixed portion.

18. The endoscope according to claim 17, wherein the movable portion has a hexagonal shape, includes a first protruding portion, a second protruding portion, and a third protruding portion that are arranged on an outer surface of the movable portion, and the first protruding portion, the second protruding portion, and the third protruding portion are arranged on surfaces different from one another, and are not adjacent to one another.

19. The endoscope according to claim 18, wherein the first protruding portion, the second protruding portion, and the third protruding portion are housed in the first rail portion, the second rail portion, and the third rail portion, respectively.

20. The endoscope according to claim 19, wherein the first protruding portion includes a first concave portion having a groove shape in which one end in a circumferential direction of the movable portion is open, and a third concave portion aligned with the first concave portion in the direction of the optical axis, the second protruding portion includes a second concave portion having a groove shape in which one end in the circumferential direction of the movable portion is open, and the first slider, the second slider, and the third slider are arranged in the first concave portion, the second concave portion, and the third concave portion, respectively.

* * * * *